United States Patent [19]

Burke, Jr. et al.

[11] Patent Number: 5,264,607
[45] Date of Patent: Nov. 23, 1993

[54] PROCESS OF MAKING BENZYLIC α,α-DIFLUROPHOSPHONATES FROM BENZYLIC α-KETOPHOSPHORATES

[75] Inventors: Terrence R. Burke, Jr., Bethesda; Benjamin B. Lim, Baltimore; Mark S. Smyth, Rockville, all of Md.

[73] Assignee: The United States of America as represented by the Secretary of the Department of Health & Human Services, Washington, D.C.

[21] Appl. No.: 897,391

[22] Filed: Jun. 12, 1992

Related U.S. Application Data

[63] Continuation-in-part of Ser. No. 767,621, Sep. 30, 1991, Pat. No. 5,200,546.

[51] Int. Cl.$^5$ ............................................. C07F 9/40
[52] U.S. Cl. ................................. 558/141; 558/204
[58] Field of Search .................................. 558/141

[56] References Cited

U.S. PATENT DOCUMENTS 4,657,899  4/1987  Rzeszotarski .................. 514/120

FOREIGN PATENT DOCUMENTS 2198134  6/1988  United Kingdom ............... 558/190

OTHER PUBLICATIONS

Fessenden et al, Organic Chemistry (1979), p. 507.
Blackburn et al, J. Chem. Soc., pp. 913–917 (1986).
Ackerman et al, J. Am. Chem. Soc., vol. 78, pp. 4444–4447 (1956).
Berlin et al, J. Org. Chem., vol. 30, pp. 1265–1267, (1965).
Berlin et al, Anal. Chem., vol. 41, pp. 1554–1559 (1969).
Gazizov et al, Zh. Obshch. Khim, vol. 48, pp. 31–32, (1970).
Pashinkin et al, Zh. Obshch. Khim, vol. 48, pp. 28–30 (1970).
Terauchi et al, Bull. Chem. Soc. Jpn., vol. 43, pp. 883–890 (1970).
Sekine et al, J. Org. Chem., vol. 45, pp. 4162–4167, (1980).
Sekine et al, Tetrahedron Lett., vol. 22, pp. 3617–3620 (1981).
Sekine et al, Chem. Lett., p. 1087 (1981).
Kume et al, J. Org. Chem., vol. 49, pp. 2139–2143 (1984).
Fujii et al, Tetrahedron Lett., vol. 26, p. 3365 (1986).
Fujii et al, Tetrahedron Lett., vol. 26, pp. 935–938 (1986).
Fujii et al, Tetrahedron, vol. 43, pp. 3395–3407 (1987).
Middleton et al, J. Org. Chem., vol. 45, pp. 2883–2887 (1988).
March, J., Advanced Organic Chemistry 3rd Ed. 1985, pp. 389.
Weast, R. C. ed. Handbook of Chemistry and Physics, F14 231-235 (1979).
Berlin et al, J. Am. Chem. Soc., vol. 86, pp. 3862–3866, (1964).
Burke et al, Synthesis, pp. 1019–1020 (1991).
Middleton, W. J., J. Org. Chem., vol. 40, pp. 574–578 (1975).

(List continued on next page.)

*Primary Examiner*—Mary C. Lee
*Assistant Examiner*—Michael G. Ambrose
*Attorney, Agent, or Firm*—Birch, Stewart, Kolasch & Birch

[57] ABSTRACT

The disclosure is concerned with providing phosphonic acid-containing derivatives of phenylalanine and optically active isomers thereof, which are functionalized in a manner which makes them suitable for facile incorporation into peptides using standard solid-phase or solution-phase techniques. The disclosure is also concerned with providing an advantageous one-step reaction method for preparing benzylic α,α-difluorophosphonates from corresponding benzylic ketophosphonates.

8 Claims, No Drawings

OTHER PUBLICATIONS

M. Hudlicky, Org. Reactions, 1988, vol. 35, pp. 513–637.

Middleton, W. J. et al, J. Org. Chem., vol. 45, pp. 2883–2887 (1980).

Blackburn, G. M. et al, J. Chem. Soc. Perkin Trans. I, pp. 1119–1125, (1984).

Blackburn, G. M. et al, J. Chem. Soc., Perkin Trans, vol. 1, pp. 913–917 (1986).

Bozell, J. J. et al, J. Org. Chem., vol. 56, pp. 2584–2587 (1991).

Glebova Z. I. et al, Zh Obshch Khim, vol. 55, pp. 1435–1437 (1985).

Burke, T. R. Jr., et al., Synthesis, vol. 11, pp. 1019–1020 (1991).

Hartman, G. D. et al, Syn. Comm. vol. 21, pp. 2103–2107 (1991).

Paquet, A. *Can. J. Chem.* 1982, 60, 976–980.

Banert, K. *Tetrahedron Lett.* 1985, 26(43), 5261–5264.

Carey, F. A. et al. *Advanced Organic Chemistry;* Second edition; Plenum: New York, 1983; p. 193.

Streitwieser, A. et al., *Introduction to Organic Chemistry;* Third edition; MacMillan: New York, 1985; pp. 737–738.

March, J. *Advanced Organic Chemistry;* John Wiley and Sons: New York, 1992; p. 909, footnote 244.

PROCESS OF MAKING BENZYLIC α,α-DIFLUROPHOSPHONATES FROM BENZYLIC α-KETOPHOSPHORATES

The present U.S. patent application is a continuation-in-part of copending U.S. patent application Ser. No. 07/767,621, filed on Sep. 30, 1991, now U.S. Pat. No. 5,200,546 which is incorporated herein by reference in its entirety.

FIELD OF THE INVENTION

The present invention is concerned with providing phosphonic acid-containing derivatives of phenylalanine and optically active isomers thereof, which are functionalized in a manner which makes them suitable for facile incorporation into peptides using standard solid-phase or solution-phase techniques. The present invention is also concerned with providing an advantageous one-step reaction method for preparing benzylic α,α-difluorophosphonates from corresponding benzylic ketophosphonates.

BACKGROUND OF THE INVENTION

Synthesis of 4-phosphonomethyl-DL-phenylalanine (Formula 1a), and derivatives thereof (Formulas 1b–d) have previously been reported [1-4] (See Table 1). The purposes of such preparations were to utilize the prepared 4-phosphonomethyl-DL-phenylalanines as competitive antagonists of N-methyl-D-aspartic acid [2] or as mimics of O-phosphotyrosine [1,3,4]. These previously prepared derivatives are not suitable for facile incorporation into peptides or peptide mimetics using standard protocols developed for either solution-phase or solid-phase peptide synthesis using "Fmoc protocols" [5,6].

Central to peptide synthesis is the protection of reactive functional groups with moieties which are easily removed under conditions which are compatible with the preservation of other functionalities in the peptide. A major branch of peptide chemistry has recently evolved using 9-fluorenylmethyloxycarbonyl (Fmoc) groups for protection of α-amino groups during coupling reactions of amino acid monomers into peptide chains. The Fmoc groups are then generally removed by brief treatment with an appropriate base such as piperidine. In such reactions, other chemically reactive groups on the amino acid monomers must be protected by functionalities which are stable to the basic conditions utilized to remove Fmoc groups. Traditionally, these other groups were removed by mild acid treatment (e.g., trifluoroacetic acid) such as used to cleave the finished peptide from a given resin. The tert-butyl group is used widely in Fmoc-bearing residues for the protection of hydroxyl groups, since it is stable to base and easily removed by mild acid treatment. Unlike the present inventive compounds, the prior known 4-phosphonomethyl-DL-phenyl-alanine compounds shown in Table 1 (Compounds 1a–1d) require significant synthetic manipulation to render them suitable for peptide synthesis.

Previously, non-benzylic α-fluorophosphonates have been converted to α,α-difluorophosphonates using electrophilic fluorinating reagents[1], and benzylic α-fluorophosphonates have been prepared from α-hydroxyphosphonates using (diethylamino)sulfur trifluoride (DAST)[10]. The conversion of α-oxoarylacetates to α,α-difluoroarylacetates using DAST[11] has also been reported.

TABLE 1

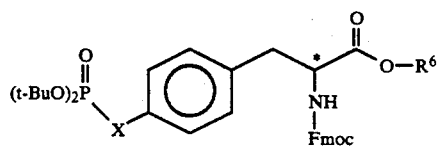

| | R¹ | R² | R³ | Ref |
|---|---|---|---|---|
| 1a | H | H | OH | 1,2,3,4 |
| 1b | Et | Bz[a] | OH | 1 |
| 1c | Et | Ac | OMe | 2 |
| 1d | H | H | HNBn[b] | 4 |

[a] Bz = benzoyl
[b] Bn = benzyl

SUMMARY OF THE INVENTION

The present invention provides novel 4-phosphonomethyl-DL-phenylalanine derivatives, analogues thereof and optical isomers thereof of the following formula:

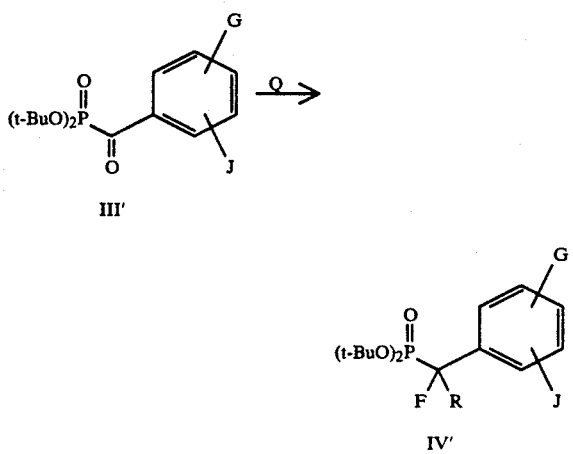

wherein t-BuO represents tertiary butoxy, Fmoc represents 9-fluorenylmethyloxycarbonyl, X is —CH₂—, —CHF—, —CF₂—, —CHOH— or —C(O)—, R⁶ is hydrogen, benzyl, pentafluorophenyl, nitrophenyl, 1-benzotriazolyl, and 1-succin-imidoyl, and * indicates a chiral carbon atom.

The compounds of Formula (I) are useful in peptide synthesis. More particularly, they are useful in preparing peptides wherein one wishes to obtain stable analogues of O-phosphotyrosine which are useful as molecular tools in biochemical studies and/or as therapeutic agents in the treatment of certain proliferative diseases.

We also provide herein an advantageous one-step reaction method for preparing benzylic α,α-difluorophosphonates of Formula IV' from corresponding benzylic ketophosphonates of Formula III'. The method is as follows:

wherein:

G and J are the same or different and are non-reaction interfering moieties; and Q is a nucleophilic fluorinating agent, e.g., (diethylamino)sulfur trifluoride (DAST) or the like.

Like the compounds of Formula (I), the compounds of Formula (IV') are useful in peptide synthesis. More specifically, they are useful in preparing peptides wherein one wishes to obtain stable analogues of 0-phosphotyrosine which are useful as molecular tools in biochemical studies and/or as therapeutic agents in the treatment of certain proliferative diseases.

DETAILED DESCRIPTION OF THE INVENTION

The following description and Example sections are provided to further aid those desiring to practice the present invention. Even so, the following sections are not to be construed as limiting to the scope of protection afforded to the present inventors in their discoveries.

As indicated in the Summary of the Invention section hereof, the present invention is concerned with providing novel 4-phosphonomethyl-DL-phenylalanine derivatives and analogues thereof, and also concerned with providing an advantageous one-step method for preparing benzylic $\alpha,\alpha$-difluorophosphonates of Formula IV' from the corresponding benzylic ketophosphonates of Formula III'. General considerations concerning each of these inventions are provided below, and thereafter, Examples relating to compounds of Formula I and their preparation as well as the inventive methods hereof, are provided.

In U.S. patent application Ser. No. 07/767,621 filed on Sep. 30, 1991, methods are provided for preparing Formula I compounds. The methods taught therein are still applicable, however, the additional methods disclosed herein are desirable in preparing certain of the present inventive compounds. This is especially true with respect to the compounds of Formula I, wherein X is —CF$_2$—. This is due to the fact that the inventors have discovered a new and highly advantageous method for preparing such compounds.

As shown in the Summary of the Invention section hereof, the present inventors can produce benzylic difluorophosphonates of Formula IV' from benzylic $\alpha$-oxophosphonates of Formula III'. The reaction method is simple and advantageous. Specifically, a compound of Formula III' is fluorinated with a nucleophilic fluorinating agent such as (diethylamino)sulfur trifluoride. However, other nucleophilic fluorinating agents may also be used if desired. In one preferred embodiment of the present invention, compounds of Formula III' are reacted under neat conditions at room temperature (about 20°–25° C.) with DAST. However, these preferred reaction conditions should not be deemed to unduly limit the present inventive discovery. The following Examples II, III and VI provide clear examples of the advantageous fluorination process provided, when a compound of Formula III' is converted to a compound of Formula IV' in a single step.

Each of the compounds of Formula III' and IV' may be substituted with substituents G and J as described above. Each of these substituents must be a non-reaction interfering moiety. Exemplary of such moieties are groups which do not adversely affect the presence of the tertiary-butoxy groups substituting the phosphorous atom. For example, substituents G and J should not be acidic substituents, or hydroxy substituted alkyls or alcohols or ketones or aldehydes in their free form. However, ester moieties may be utilized if so desired, and exemplary of suitable non-interfering substituents for G and J are hydrogen, halogen (F, Cl, Br and I), C$_{1-8}$ alkyl, halogen substituted C$_{1-8}$ alkyl, and other accepted groups such as provided for in the Examples hereof.

Regarding the preparation of compounds of Formula III', $\alpha$-oxophosphonates are normally prepared by the michaelis-arbuzov reaction of acyl chlorides with trialkyl phosphites, [17,18]. Nonetheless, we found that high yields of the desired $\alpha$-oxophosphonates of Formula III' can be obtained by the oxidation of corresponding $\alpha$-hydroxyphosphonates of Formula II' employing a variety of oxidizing agents.

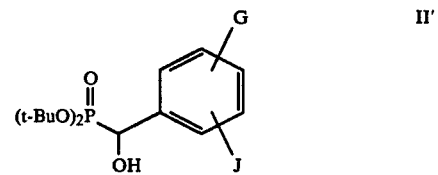

In Formula II' G and J are the same or different and are non-reaction interfering moieties as defined above with respect to Formula IV', however, with the additional consideration that G and J may contain an unprotected tertiary hydroxy substituent.

In proceeding from a compound of Formula II' to III', MnO$_2$ provided high yields of the desired $\alpha$-oxophosphonates. However, other oxidizing agents including pyridinium dichromate, pyridinium chlorochromate, dichloro dicyanobenzoquinone (DDQ) and Swern oxidation were also found to yield the desired $\alpha$-oxophosphonates of Formula III'.

We note that when phosphite esters other than tertiary-butyl (i.e., methyl or benzyl) were utilized instead of the t-butyl substituent occurring on compounds of Formula II', such groups were incompatible with the reaction transformation. Specifically, reversion of the hydroxyphosphonate to the aldehyde resulted. Additionally, we note that an oxidizing method of preparing compounds of Formula III' requires that G and J not be hydroxy groups or hydroxy substituted moieties (other than tertiary hydroxy) during oxidation of the corresponding $\alpha$-hydroxyphosphonate. However, G and J may contain protected hydroxy substituents if desired, which are later deprotected (after oxidation of the $\alpha$-hydroxyphosphonate) to give a Formula III' compound having a G and/or J substituent comprising a hydroxy or hydroxy substituted moiety.

EXAMPLES

The following Examples are provided to illustrate certain embodiments and advantages associated with the present discoveries.

Specifically regarding each of the Examples provided below, the following comments are thought appropriate.

Example I—As indicated in the Example, central to the synthesis of the compound provided is the aldol condensation of ethyl $\alpha$-azidoacetate with 4-[bis(tert-butyl)phosphonomethyl]-benzaldehyde to yield vinyl azide. The synthesis method provided in Example I, as well as those provided in U.S. patent application Ser. No. 07/767,621, filed on Sep. 30, 1991, provide the basis for many of the other reactions set forth in the present application.

Example II—This Example provides a general process for the synthesis of benzylic difluorophosphonates. In the Example, each of G and J are hydrogen. However, this should not be deemed to limit the present inventive discovery since G and J may be other non-reaction interfering moieties, if so desired.

Regarding the procedure utilized in Example II, we initially sought to prepare benzylic α,α-difluorophosphonates from the corresponding benzylic α-hydroxy phosphonates through the intermediacy of the α-fluorophosphonates. While this appeared particularly appealing since benzylic α-hydroxyphosphonates are easily obtained by the reaction of aldehydes with dialkyl phosphites under alkaline conditions[12], we were unable to convert the benzylic monofluoro to the difluorophosphonates by this approach. Based with this fact, we postulated that it might be possible to convert benzylic α-oxophosphonates to the corresponding benzylic α,α-difluorophosphonates. Accordingly, we arrived at the inventive method for preparing α,α-difluorophosphonates from the corresponding α-oxophosphonates shown in Example II.

Example III—The Example provides for the synthesis of a difluorophosphonomethyl phenylalanine compound (compound 14). In proceeding from compound 10 to compound 11, the method utilizes the novel fluorination step discussed above. Of the compounds shown in Reaction Scheme II, provided in Example III, the compounds numbered 11, 12, 13 and 14 are novel.

Example IV—In this Example, a hydroxy phosphonomethyl phenylalanine compound encompassed by Formula (I) is prepared. The compound is prepared using a direct modification of the synthesis provided in Example I. Compounds 8, 15 and 16 are novel compounds.

Example V—In the Example, a monofluorophosphonomethyl phenylalanine compound encompassed by Formula I is prepared from the corresponding α-hydroxyphosphonate utilizing a nucleophilic fluorinating agent (i.e., DAST).

Example VI—This Example provides an alternative synthesis method for preparing difluorophosphonomethyl phenylalanine compounds encompassed by Formula (I). In the synthesis scheme provided (i.e., VI), the synthesis of compound 27 is analogous to that outlined in Scheme I for the preparation of difluorophosphonate 4', except that 4-bromobenzaldehyde (24) is used rather than the benzaldehyde (1'). Each of the compounds shown in Scheme VI is novel, except for starting compound 24.

Example VII—Compound 1o is prepared based on the inventors' discovery that the corresponding hydroxyphosphono methyl phenylalanine compound 9 can be oxidized to give compound 10. Previous methods of preparing ketophosphonates have relied on the reaction of an appropriate acid chloride with either a trialkylphosphite or the anion of a dialkyl phosphite.

A. Preparation of Phosphomethyl Phenylalanine Compounds

As disclosed in U.S. patent application Ser. No. 07/767,621 filed on Sep. 30, 1991 a specific example of the synthesis of a Formula I compound wherein X=$CH_2$ is as follows.

EXAMPLE I

4[Bis(t=butyl)phosphonomethyl]-N-Fmoc-DL-phenylalanine

Synthesis Overview

Central to the synthesis of the title compound (compound No. 4 in the synthesis below) is the aldol condensation of ethyl α-azidoacetate [7] with 4-[bis(tert-butyl)-phosphonomethyl]-benzaldehyde (compound to 1) to yield vinyl azide (compound No. 2) (74%). The vinyl azide (compound No. 2) is key to the synthetic route as the tert-butyl groups thereof are retained under the mild conditions (2.8 bar $H_{2/10\%}$ Pd.C) employed to effect transformation to the amino ester (compound No. 3). Finally, hydrolysis of the methyl ester with concomitant introduction of the Fmoc-amino protection to yield compound No. 4 is achieved by sequentially treating compound 3 with 1N sodium hydroxide (20 min.) and thereafter adjusting the pH to 8 by introducing carbon dioxide and allowing the mixture to react overnight with 1-benzotriazolyl-9-fluorenyl-methyl carbonate (Fmoc-OBT).[8] The final product (compound No. 4) is obtained as a white powder (48% overall yield).

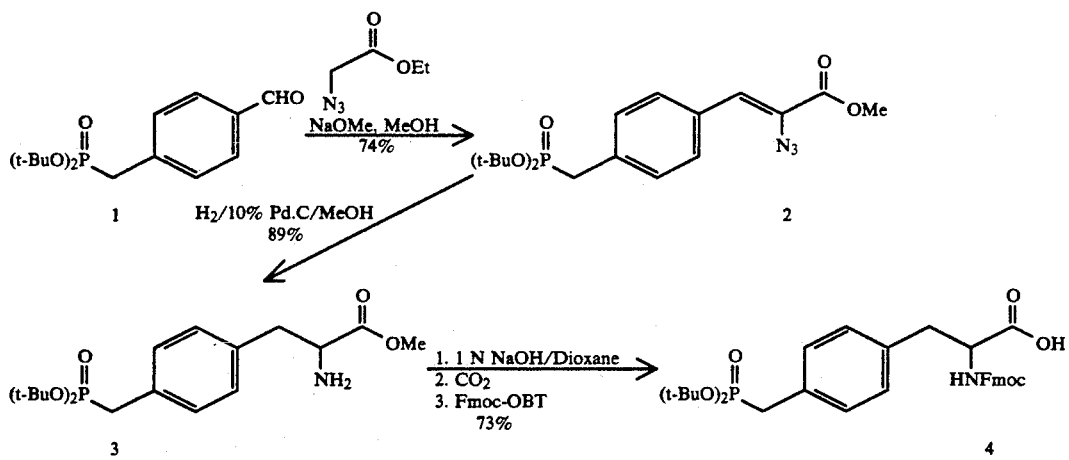

Compound Preparation

α-Azido-4-[bis(tert-butyl)phosphonomethyl]cinnamic acid methyl ester (Compound No. 2)

To a cold (−30° C.) solution of 4-[bis(tertbutyl)phosphonomethyl]benzaldehyde (compound No. 1, 3.12 g, 10 mmol) and ethyl α-azidoacetate (12.90 g, 100 mmol, 10 equiv.) in anhydrous MeOH (50 mL) is added a solution of 5.4M NaOMe (14.8 mL, 80 mmol, 8 equiv.) over 2 minutes under argon with stirring. The colorless reaction mixture is stirred at 2° C. for 1 hour, then diluted with brine (300 mL); extracted with Et$_2$O (3×100 mL); dried (MgSO$_4$) and Et$_2$O removed. The resultant colorless oil is dissolved in pet.ether (30 mL), cooled to −78° C., then warmed to 0° C. with mixing to yield a white crystalline solid. The solid is treated with ice-cold petroleum ether/Et$_2$O (30:1, 30 ml), filtered and dried; yield 2.86g (74%); mp 109°-111° C. C$_{19}$H$_{28}$N$_3$O$_5$P MW 409 (compound is too unstable for combustion analysis). FABMS:m/z=410 (M+1).

IR (KBr) ν=2980, 2124, 1707, 1439, 1369, 1330 cm. $^1$H-NMR (200 MHz, CDCl$_3$)=1.42 (s, 18H, 2t-C$_4$H$_9$), 3.05 (d, 2H, J=22 Hz, P-CH$_2$), 3.90 (s. 3H, OCH$_3$), 6.90 (s, 1H, vinylic), 7.28 (dd, 2H, J=2 Hz & 8 Hz, ArH$_{3\&5}$), 7.74 (d, 2H, J=8 Hz, ArH$_{2\&6}$).

4-[Bis(tert-butyl)phosphonomethyl]-D,L-phenylalanine methyl ester (Compound No. 3)

A solution of compound 2 (4.50 g, 110 mmol) in MeOH (30 mL) is shaken in a Parr apparatus (2.8 bar H$_2$) over 10%Pd.C (1.10 g) for hour at room temperature. Filtration through Celite filter and removal of solvent yields compound No. 3 as an oil: 3.75 g (89%).

| | | | | |
|---|---|---|---|---|
| C$_{19}$H$_{32}$NO$_5$P.¼H$_2$O | calc. | C 57.20 | H 8.46 | N 3.51 |
| (385) | found | C 57.23 | H 8.14 | N 3.55 |

FABMS: m/z=386 (M+1)

IR (film) ν=3853, 3383, 2979, 1739, 1653, 1558, 1540, 1514, 1456, 1394, 1369 cm$^{-1}$. $^1$H-NMR (250 MHz, CDCl$_3$):δ=1.42 (s, 18H, 2t-C$_4$H$_9$), 1.66 (br s, 2H, NH$_2$), 2.86 (dd, 1H,J=8 Hz and 13 Hz, H$_{\beta 1}$), 3.01 (d,2H, J=21 Hz, P-CH$_2$), 3.06 (dd, 1H, J=5 Hz and 13 Hz, H$_{\beta 2}$), 3.70 (s, 3H, OCH$_3$), 3.72 (dd, 1H, J=5 Hz and 8 Hz, H$_{60}$), 7.11 (d, 2H, J=8 Hz, ArH$_2$ $_{and}$ $_6$), 7.22 (dd, 2H, J=2 Hz and 8 Hz, ArH$_3$ $_{and}$ $_5$). Structural assignments were supported by $^{13}$C-NMR and DEPT experiments.

4-[Bis(tert-butyl)phosphonomethyl]-N-Fmoc-DL-phenylalanine (Compound No. 4)

A solution of amine compound No. 3 (770 mg, 1.93 mmol) in dioxane (10 mL) is stirred at room temperature 20 min) with aqueous 1 N NaOH (10 mL, 10 mmol, 5 equiv.). Carbon dioxide is then bubbled in (resulting pH 8.0-8.5) and Fmoc-OBT (857 mg. 2.40 mmol, 1.2 equiv) is added as a suspension in dioxane (3×10 mL) and stirred overnight at ambient temperature. The reaction mixture is partitioned between cold aqueous 5% citric acid (200 mL) and CHCl$_3$ (3×100 mL); the combined organic is washed with cold 5% citric acid (1×100 mL); brine (1×200 mL); dried (MgSO$_4$) and taken to dryness, yielding a light yellow resin (1.92g). The resin is taken up in CHCl$_3$ and filtered through a silica pad. Unreacted Fmoc-OBT and faster impurities are removed with CHCl$_3$ (5×100 mL) with product then being eluted (8×100 mL) with 1% EtOH in CHCl$_3$ and taken to dryness, providing a foam (953 mg) which is dissolved in Et$_2$O (5 mL) and cooled with petroleum ether (20 mL) to yield compound No. 4 as a white powder: 835 mg (73%); mp 65°-70° C. (gas, dec.).

| | | | | |
|---|---|---|---|---|
| C$_{33}$H$_{40}$NO$_7$P | calc. | C 66.77 | H 6.79 | N 2.36 |
| (593) | found | 67.08 | 7.26 | 2.32 |

FABMS: m/z=594 (M+1).

IR (film) ν=2979, 1721, 1513, 1450, 1370 cm$^{-1}$. $^1$H-NMR (250 MHz, CDCl$_3$):=1.31 (s, 9H,t-C$_4$H$_9$), 1.38 (s, 9H,t-C$_4$H$_9$), 3.01 (dd, 1H, J=14 Hz and 22 Hz, P-C-H$_\alpha$), 3.13 (dd, 1H, J=14 Hz and 22 Hz, P-C-H:), 3.18 (M, 1H, H$_{\beta 1}$), 3.29 (m, 1H, H$_{\beta 2}$), 4.22 (t, 1H, J=7 Hz, OC-H), 4.32 (dd , 1H, J =7 Hz and 10 Hz, NCO2C-H° ), 4.48 (dd., 1H, J=7 Hz and 10 Hz, NCO2C-H$_\alpha$, 4.68 (m, 1H, NC-H), 5.40 (d, 1H, J=7 Hz, N-H), 7.12 (d, 2H, J=8 Hz, ArH$_2$ $_{and}$ $_6$), 7.20 (dd, 2H, J=2 Hz and 8 Hz, ArH$_3$ $_{and}$ $_5$) , 7.30 (dt$^b$, 2H, J=4 Hz and 7 Hz, fluor.-H$_2$ $_{and}$ $_7$)$^c$, 7.39 (t$^b$, 2H, J=7 Hz, fluor.-H$_3$ $_{and}$ $_6$)$^c$, 7.59 (br dd., 2H, J=4 Hz and 7 Hz, fluor.-H$_4$ $_{and}$ $_5$)$^d$, 7.76 (br d, 2H, J=7 Hz, fluor.-H$_1$ $_{and}$ $_8$)$^d$. Structural assignments were supported by $^1$H-$^1$H COSY and $^{13}$C-NMR.

$^a$ coupling pattern is distorted;
$^b$ coupling pattern is apparent;
$^c$ assignments may be reversed; and
$^d$ assignments may be reversed.

B. Preparation of Benzylic Difluoroohosohonates

Exemplary of our general process for the synthesis of benzylic difluorophosphonates is the synthesis of 5'. The process is concerned with the preparation of protected benzylic difluorophosphonates (i.e., 4') by fluorinating the corresponding ketophosphonates (3'). Typical of fluorinating reagents which will accomplish this transformation is (diethylamino)sulfur trifluoride (DAST), However, it is envisioned that other nucleophilic fluorinating agents would also be appropriate. The ketophosphonates can either be prepared by known procedures (for example, the reaction of acid chlorides with either trialkyl phosphites or anions of dialkyl phosphites) or can be prepared from hydroxyphosphonates (2') by oxidation with any of several oxidizing agents. We have found that MnO$_2$, pyridinium dichromate, dichlorodicyanoquinone (DDQ) and the Swern oxidation (dimethyl sulfoxide, oxalyl chloride and triethylamine) all accomplish this oxidation. It is anticipated that several other standard oxidizing agents would also work. Our preparation herein of ketophosphonates by oxidation of the corresponding hydroxyphosphonate (i.e., 2'-3') is novel, and is included as an inventive process in this disclosure.

Scheme I

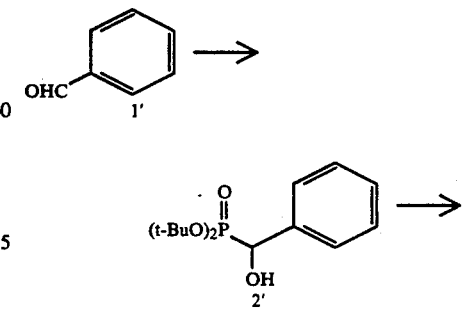

-continued
Scheme I

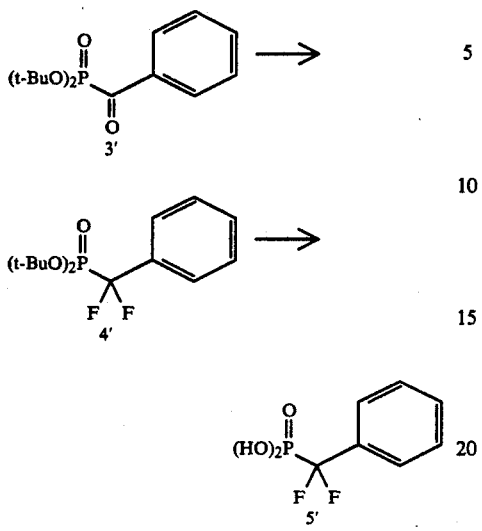

Typical conditions for the preparation of the benzylic difluorophosphonate 5' are:

Preparation of benzylic α-hydroxyphosphonate, 2'.

To an ice-cold stirred suspension of NaH (1.2 equiv.; 0.3M in THF) is added a solution of di tert-butyl phosphite (1.2 equiv.; 0.3M in THF) over 5 minutes and the mixture stirred under argon at 0° C. (0.5 hr). A solution of aldehyde 1' equiv.; 1M in THF) is rapidly added and the reaction is then stirred at room temperature (1.5 hr). The reaction is quenched (H$_2$O), subjected to an extractive workup (brine/CHCl$_3$) and purified by silica gel chromatography, yielding pure benzylic α-hydroxyphosphonate 2' (86%), mp 110°-113° C. (gas).

Preparation of benzylic α-ketophosphonate, 3'.

A solution of benzylic α-hydroxyphosphonate 2, (15 mM in toluene) is stirred at reflux with activated MnO$_2$ 10 equiv.; 1.5 hr). The reaction mixture is cooled (0° C.), filtered through celite, taken to dryness and purified by silica gel chromatography to yield pure benzylic α-ketophosphonate 3' (87%), oil.

Conversion of benzylic ketophosphonate 3, to benzylic α,α-difluorophosphonate, 4'.

A solution of benzylic α-ketophosphonate 3' (0.5M in DAST) is stirred at room temperature overnight under argon. It is then cooled (0° C.), diluted with CHCl$_3$, added dropwise to cold (0° C.) concentrated KOH, then subjected to an extractive work up and purified by silica gel chromatography to yield pure benzylic difluorophosphonate 4' (79%), oil.

Ester hydrolysis [conversion to benzylic α,α-difluorophosphonic acid, 5'].

A solution of di-tert-butyl difluorophosphonate 4' [100 mM in trifluoroacetic acid (TFA)] is stirred at room temperature (1.5 hr) with anisole (5 equiv.). Excess TFA is blown off under argon (gentle warming), with residual traces of TFA being removed under high vacuum. The resulting crude difluorophosphonic acid is crystallized from CHCl$_3$: pet.ether to yield benzylic α,α-difluorophosphonic acid 5' (61%), mp 109°-111° C. (gas; soften 106° C.).

B. Synthesis of the difluorophosphonomethyl phenylalanine 14

Scheme II

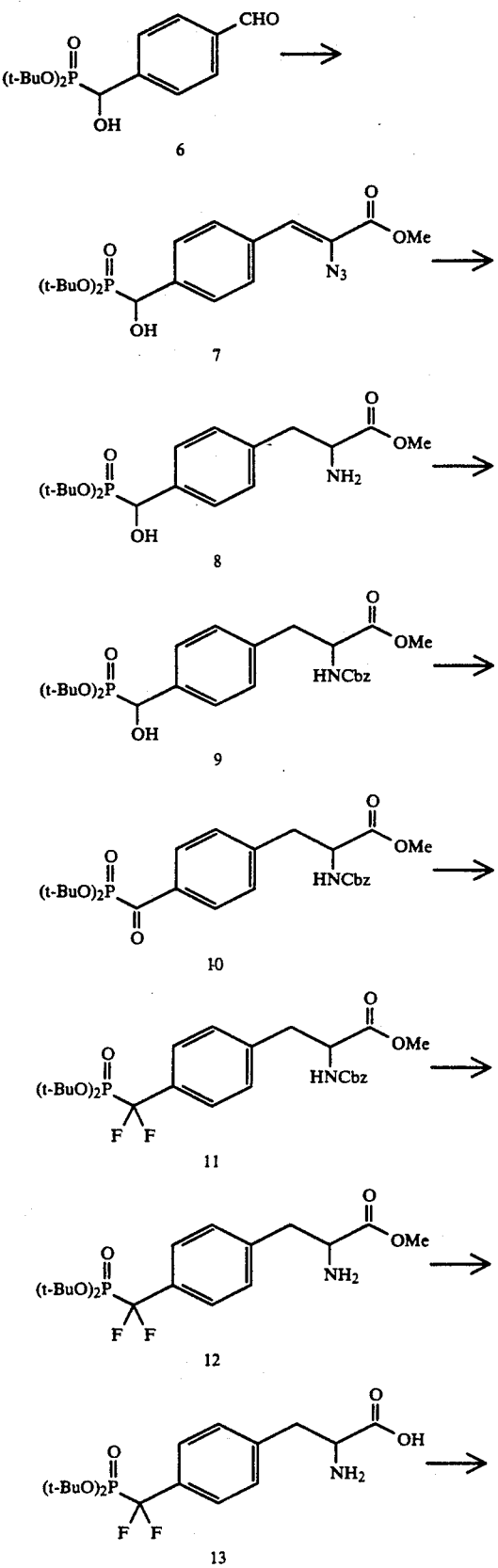

-continued
Scheme II

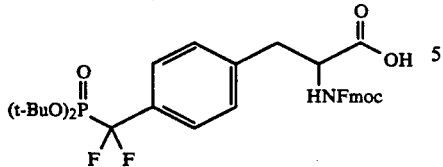

The general process of Example I and the process for preparing benzylic difluorophosphonates outlined in Scheme I of Example II, were applied to the preparation of the difluorophosphonomethyl phenylalanine 14, as shown in Scheme II. In Scheme II "Cbz" indicates a benzyloxycarbonyl group, and "Fmoc" indicates a fluoren-9-yl-methyloxycarbonyl group.

Experimental conditions for this preparation are given below:

Methyl α-azido-4-[bis(tert-butoxy)phosphorylhydroxymethyl]-cinnamate, 7.

To a solution of 6.45 g (50 mmol) of ethyl α-azidoacetate and 1.64 g (5.0 mmol) of 4-[bis(tert-butoxy)-phosphorylhydroxymethyl)benzaldehyde 6 in MeOH (20 mL) at −78° C. was added a total of 7.4 mL (40 mmol) of NaOMe, 5.4M in MeOH, dropwise over 5 minutes. The mixture was stirred 5 minutes at −78° C. then an additional 1 hour at 0° C. The resulting light yellow suspension was subjected to an extractive work up (brine/EtOAc) to yield a light yellow crystalline solid, which was triturated with $CHCl_3$/pet. ether (35°–60° C.) to yield 7 as light yellow crystals, 1.26 g (57%), mp 111°–113° C.

Methyl 4-[bis(tert-butoxy)phosphorylhydroxymethyl]-D,L-phenylalaninate, 8.

A solution of 7 (1.25 g, 2.85 mmol) in MeOH (50 mL) was hydrogenated in a Parr apparatus over 10% Pd.C (200 mg) under 40 psi $H_2$. The hydrogen was replenished after 10 minutes. The reaction was terminated after 3 hours, and catalyst removed by filtration. Evaporation of solvent yielded 8 as a clear, colorless syrup, 1.17 g (100% crude yield). Silica gel chromatography [$CHCl_3$:MeOH(25:1)] provided pure 8 (92%).

Methyl 4-[bis(tert-butoxy)phosphorylhydroxymethyl]-N-(benzyloxycarbonyl)-D,L-phenylalaninate, 9.

To a solution of 8 (876 mg, 2.18 mmol) in THF (22 mL) at 0° C. was added $NEt_3$ 1.22 mL, 8.74 mmol), followed by benzyl chloroformate (0.34 mL, 2.40 mmol) dropwise via syringe. The reaction was stirred at 0° C. for 0.5 hours, then diluted with $Et_2O$ (20 mL) and quenched by dropwise addition of brine (1 mL). Additional brine (20 mL) was added and the organic phase separated and combined with an $Et_2O$ extract (2×20 mL) of the residual brine. The combined $Et_2O$ was dried ($MgSO_4$), filtered and solvent removed by rotary evaporation under reduced pressure to yield crude 9 (1.03 g, 88%). Silica gel chromatography [EtOAc/hexanes (4:3)] provided pure 9 (621 mg, 53%).

Methyl 4-[bis(tert-butoxy)phosphorylcarbonyl]-N-(benzyloxycarbonyl)-D,L-phenylalaninate, 10.

To a solution of 9 (125 mg, 0.23 mmol) in $CHCl_3$ (1 mL) was added celite (200 mg) and freshly activated 4A molecular sieves (230 mg). Pyridinium dichromate (219 mg, 0.58 mmol) was added and the mixture stirred at ambient temperature (4 hours). The reaction was diluted with EtOAc (5 mL) and filtered through a pad of Florisil (TLC grade). The Florisil was rinsed with EtOAc (30 mL) and combined filtrates taken to dryness by rotary evaporation under reduced pressure to afford crude 10 (85 mg, 70%). Silica gel chromatography [EtOAc/hexanes (1:1)] provided pure 10 (77 mg, 62%).

Methyl 4-[bis(tert-butoxy)phosphoryldifluoromethyl]-N-(benzyloxycarbonyl)-D,L-phenylalaninate, 11.

To ketophosphonate 10 (490 mg, 0.92 mmol) was added (diethylamino)sulfu trifluoride (DAST) (1.8 mL) and the mixture stirred overnight at ambient temperature. The reaction mixture was cooled (0° C.), diluted with $CHCl_3$ (5 mL) and added dropwise to a cold, well stirred solution of saturated aqueous $NaHCO_3$ (20 mL). The mixture was extracted with $CHCl_3$ (2×20 mL), dried ($MgSO_4$) and solvent removed by rotary evaporation under reduced pressure to yield crude 11 (665 mg). The crude product Was immediately purified by silica gel chromatography EtOAc/hexanes (1:2)] to provide pure 11 (274 mg, 54%).

Methyl 4-[bis(tert-butoxy)phosphoryldifluoromethyl]-D,L-phenylalaninate, 12.

A solution of benzyloxycarbonyl-protected 11 (45 mg, 0.081 mmol) in MeOH (0.8 mL) is stirred at ambient temperature under 1 atm of $H_2$ over 10% Pd C (9 mg). After 2.5 hours the reaction mixture is filtered through silica gel and taken to dryness in vacuo to yield crude 12 quantitatively. Pure 12 (60% yield) can be obtained by silica gel chromatography [$CHCl_3$:MeOH(20:1)].

4-[Bis(tert-butoxy)phosphoryldifluoromethyl]-N-(fluoren-9-ylmethoxycarbonyl)-D,L-phenylalanine, 14.

To a solution of amino ester 12 (15 mg, 0.036 mmol) in dioxane (0.5 mL) is added 1 N NaOH (0.18 mL) and the reaction is stirred at ambient temperature. After 20 minutes $CO_2$ gas is bubbled into the reaction for 5 minutes, then solid Fmoc-OBt (15 mg, 0.043 mmol) is added and stirring continued for 1 hour. Cold 5% citric acid (10 mL) is added and the mixture is extracted with CHCl' (3×10 mL); the combined extracts are dried ($MgSO_4$) and the solvent evaporated in vacuo to yield crude 14 (13.7 mg, 60%).

C. Preparation of hyroxyphosphonomethyl phenylalanines

Example IV

Hydroxyphosphonomethyl phenylalanines are prepared using a direct modification of the synthesis provided in Example I. Specifically, compound 8 in Reaction Scheme III is substituted for compound 3 in Example I.

Scheme III

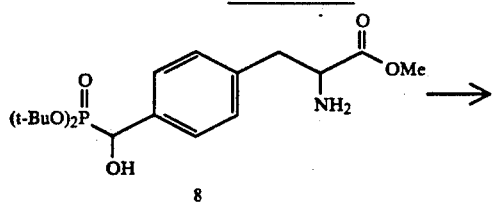

4-[bis(tert-Butoxy)phosphorylhydroxymethyl]-N-(fluoren9-ylmethoxycarbonyl)-D,L-phenylalaninate (16).

A solution of compound 8 (410 mg, 1.02 mmol) in dioxane (10 mL) is treated with 1 N NaOH (5.1 mL, 5 eq.) and stirred at ambient temperature (0.5 h), yielding a solution of crude 4-[bis(tert-Butoxy)phosphorylhydroxymethyl]-D,L-phenylalanine (15), which is not isolated. The pH is adjusted to 8 by bubbling in $CO_2$ gas, Fmoc-OBT (402 mg, 1.12 mmol) is added and the mixture stirred at ambient temperature (3.5 hours). Ice-cold 5% citric acid (25 mL) is added and the resultant solution is extracted with $CHCl_3$ (3 × 30 mL). The combined extracts are dried ($MgSO_4$) and evaporated under reduced pressure to yield crude 16. Purification by silica gel chromatography affords pure 16 as a colorless foam (277 mg, 44%).

D. Preparation of Monofluorophosphonomethyl phenylalanines

Example V

Previously, benzylic α-fluorophosphonates have been prepared from α-hydroxyphosphonates using DAST[13]. We have essentially applied this general chemical transformation to the specific compound 9, leading to monofluorophosphonomethyl phenylalanines 20–23 (Scheme V).

Scheme V

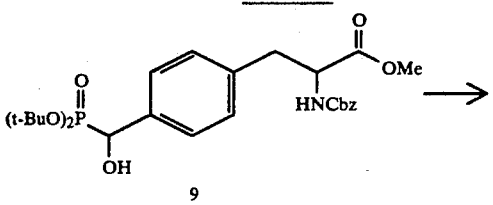

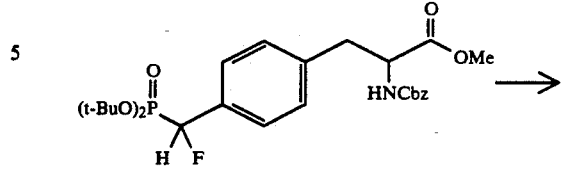

Preparation of 23 proceeds from 20 as already described in Example III for the transformation of 11 to 14. Conversion of 9 to 20 applies to this specific case the known transformation of benzylic hydroxyphosphonates to the corresponding monofluorophosphonates.[13]

Methyl 4-[bis(tert-Butoxy)phosphoryl-fluoromethyl]-N-(benzyloxycarbonyl)-D,L-phenylalaninate (20).

To DAST (0.15 mL, 1.1 mmol) in anhydrous $CHCl_3$ (0.6 mL) at −78° C. is slowly added compound 9 (536 mg, 1.0 mmol) in $CHCl_3$ (2.0 mL). After 10 minutes, the reaction mixture is warmed to ambient temperature and stirred (20 minutes). The mixture is slowly diluted with brine (10 mL) then extracted with $CHCl_3$ (2 × 10 mL) and the combined extracts dried ($MgSO_4$) and evaporated under reduced pressure to yield crude 20 (629 mg). Purification by silica gel chromatography affords pure 20 as a syrup (295 mg, 55%).

Methyl 4-[bis(tert-Butoxy)phosphoryl-fluoromethyl]-D,L-phenylalaninate (21).

Compound 20 (1.09 g, 2.03 mmol) in anhydrous MeOH (50 mL) is hydrogenated over 10% Pd.C (436 mg) under $H_2$ (45 psi) in a Parr apparatus. The vessel is evacuated and replenished with $H_2$ at approximately 30 minute intervals. After 4 hours, the mixture is removed, filtered through celite and solvent removed under reduced pressure, yielding crude 21 (813 mg). Purification by silica gel chromatography affords pure 21 (694 mg, 85%).

4-[bis(tert-Butoxy)phosphoryl-fluoromethyl]-N-(fluoren-9-ylmethoxycarbonyl)-D,L-phenylalaninate (23).

To compound 21 (690 mg, 1.71 mmol) in dioxane (17 mL) is added 1N NaOH (8.6 mL, 5 eq.) and stirred at ambient temperature (25 minutes), yielding a solution of crude 4-[bis(tert-Butoxy)phosphoryl-fluoromethyl]-D,L-phenylalanine (22), which is not isolated. The pH is adjusted to 8 by bubbling in $CO_2$ gas, Fmoc-OBT (673 mg, 1.88 mmol) is added and the mixture stirred at ambient temperature (3 hours). Ice-cold 5% citric acid (30 mL) is added and the resultant solution is extracted with $CHCl_3$ (3×30 mL). The combined extracts are dried ($MgSO_4$) and evaporated under reduced pressure to yield crude 23 (1.48 g). Purification by silica gel chromatography affords pure 23 as a colorless foam (407 mg, 40%).

E. Alternative Synthesis Methods for Synthesizing Difluorophosphonomethyl Phenylalanines

Example VI

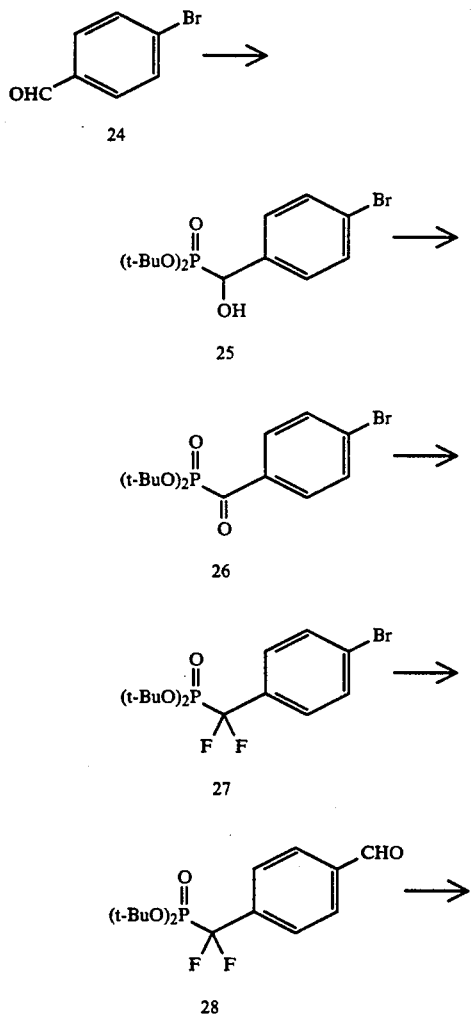

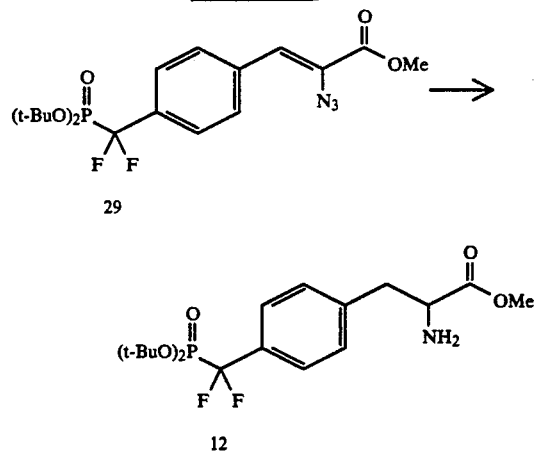

The synthesis of key intermediate 27 is similar to that already described for the synthesis of unsubstituted 4' (Example II). It should be noted, however, that oxidation of bromo hydroxyphosphonate 25 to bromo ketophosphonate 26 must be conducted under milder conditions (pyridinium dichromate 0° C. to room temperature) than those used to oxidize unsubstituted hydroxyphosphonate 2' ($MnO_2$ in refluxing toluene) to avoid decomposition back to the starting aldehyde 24. Transformation of 27 to yield benzaldehyde 28 can be achieved by a number of literature procedures.[14,15] Once formed, aldehyde 28 can be converted to amino ester 12 using transformations similar to those reported herein (Scheme II) and as disclosed in U.S. application Ser. No. 07/767,621.

4-[bis(tert-Butyl)phosphoryl hydroxymethyl]-bromobenzene (25).

To a stirred suspension of NaH, 80% in oil (3.60 g, 2.88 g NaH, 120 mmol) in anhydrous THF (100 mL) at 0° C. is added tert-butyl phosphite (23.3 g, 120 mmol) dropwise over 5 minutes, and the mixture stirred at 0° C. (30 minutes). A solution of 4-bromobenzaldehyde (14.52 g, 78 mmol) in anhydrous THF is added rapidly and the mixture stirred at 0° C. (1 hour). The reaction mixture is diluted with $H_2O$ (400 mL), extracted with $CHCl_3$ (1×100 mL) then EtOAc (2×100 mL) and the combined extracts washed with $H_2O$ (1×200 mL), dried ($MgSO_4$) and evaporated under reduced pressure to yield crude 25 as a white crystalline solid. Trituration with pet. ether provides 25 as white crystals (23.92 g, 81%); mp 126.0°-126.5° C.

4-[bis(tert-Butyl)phosphoryloarbonyl]-bromobenzene (26).

To a solution of 25 (16.41 g, 43.3 mmol) in anhydrous $CH_2Cl_2$ (300 mL) at 0° C is added pyridinium dichromate (40.7 g, 108 mmol, 2.5 eq.) and the suspension stirred overnight, coming to ambient temperature gradually. The crude mixture is filtered through a 6.5 cm dia×4 cm high pad of florisil having a layer of celite on top, and the pad washed with EtOAc (3×100 mL). The combined filtrates were taken to dryness under reduced pressure to yield z6 as a clear, light brown oil (13.89 g, 86%).

4-[bis(tert-Butyl)phosphoryl difluoromethyl]-bromobenzene (27).

To 26 (12.2 g, 32.4 mmol) is added DAST (8.6 mL, 10.4 g, 64.8 mmol, 2 eq.) over 5 minutes at 0° C. The reaction is then stirred overnight, gradually coming to ambient temperature. The mixture is diluted with CHCl$_3$ (30 mL), cooled and added to a well-stirred solution of NaHCO$_3$ 32.7 g, 390 mmol) in H$_2$O (300 mL) at 0° C. The resulting mixture is stirred (5 minutes), then extracted with CHCl$_3$ (3×100 mL); the combined organic washed with aqueous NaHCO, (1×300 mL); dried (MgSO$_4$) and evaporated under reduced pressure to yield crude 27 as a brown oil (12.20 g). Purification by silica gel chromatography affords pure 27 as a light yellow oil (694 mg, 85%).

4-[bis(tert-Butyl)phosphoryl difluoromethyl]-benzaldehyde (28).

To compound z7 (50 mg, 0.12 mmol) in anhydrous ether (0.63 mL) at −78° C. under argon is added n-BuLi (1.6M in hexanes, 0.12 mL, 0.19 mmol) and the mixture stirred at −78° C. (20 minutes). A solution of ethyl formate, 1M in ether (0.25 mmol, 2 eq.) is added and the mixture stirred (0.5 hours at −78° C). Saturated aqueous NH$_4$Cl (1 mL) is added and the mixture warmed to ambient temperature and extracted with ether (3×1 mL). The combined extracts are dried (MgSO$_4$) and taken to dryness under reduced pressure, affording 43 mg of crude 28, however, contaminated with starting material 27.

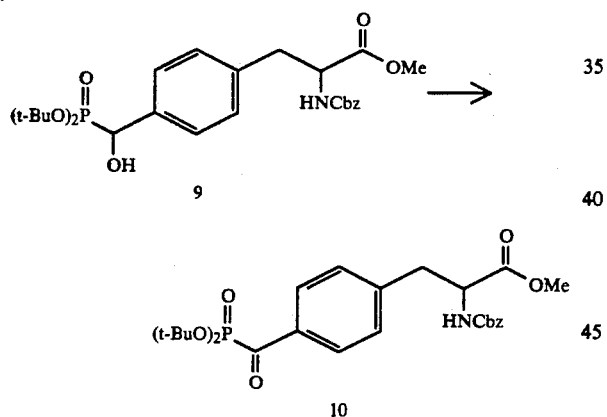

compound 10 is prepared based on the inventors' discovery that the corresponding hydroxyphosphono methyl phenylalanine compound 9 can be oxidized to give compound 10.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Each of the publications and patents referred to herein above are expressly incorporated herein by reference in their entirety.

REFERENCES

1. Marseigne, I.; Roques, B. P. Synthesis of new amino acids mimicking sulfated and phosphorylated tyrosine residues. J. Org. Chem., 1988, 53, 3621-3624.
2. Bigge, C. F.; Drummond, J. T.; Johnson, G.; Malone, T.; Probert, A. W., Jr.; Marcoux, F. W.; Coughenour, L. L.; Brahce, L. J. Exploration of phenyl-spaced 2-amino-(5,9)-phosphonoalkanoic acids as competitive N-methyl-D-aspartic acid antagonists. J. Med. Chem., 1989, 32, 1580-1590.
3. Bayle-Lacoste, M.; Moulines, J.; Collignon, N.; Boumekouez, A.; de Tinguy-Moreaud, E.; Neuzil, E. Synthesis of 4-phosphono-DL-phenylalanine and of 4-(phosphonomethyl)-DL-phenylalanine, two analogues of O-phosphotyrosine. Tetrahedron, 1990, 46, 7793-7802.
4. Roques, B. P.; Marseigne, I.; Charpentier, B. Preparation of amino acids and tyrosine-containing peptides as drugs and pharmaceutical compositions containing them. Eur. Pat. Appl. EP 354 10 (CA 113: 78979x), 1990.
5. Carpino, L. A.; Han, G. Y. The 9-fluorenylmethoxycarbonyl function, a new base-sensitive amino-protecting group, J. Amer. Chem. Soc., 1970, 92, 5748-5749.
6. Burke, T. R.; Knight, M.; Chandrasekhar, B. Solid-phase synthesis of viscosin, a cyclic depsipeptide with antibacterial and antiviral properties. Tetrahedron Letters, 1989, 30, 519-522.
7. Hemetsberger, H.; Knittel, D.; Weidmann, H. Montgh. Chem., 1969, 100, 1599-1603.
8. Paquet, A. Can. J. Chem., 1982, 60, 976-80.
9. Sealock, R.R. D-Tyrosine in Biochemical Preparations, Vol. I, John Wiley & Sons, Inc., London, England, (H. E. Carter, Ed.), 1949, 71-74.
10. Yang, Z. Y.; Burton, D. J. A novel, general method for the preparation of α,α-difluoro functionalized phosphonates, Tetrahedron Lett., 1991, 32 1019-1022.
11. Middleton, W. J.; Bingham, E. M. α,α-Difluoroarylacetic acids: Preparation from (diethylamino) sulfur trifluoride and α-oxoarylacetates. J. Org. Chem., 1980, 45, 2883-2887.
12. Burke, T. R. Jr., Li, Z. H.; Bolen, J. B.; Marquez, V. E. Phosphate-containing inhibitors of tyrosine-specific protein kinases. J. Med. Chem., 1991, 34 1577-1581.
13. Blackburn, G. M.; Kent, D. E. Synthesis of alpha- and gamma-fluoroalkylphosphonates. J. Chem. Soc. Perkin. Trans. 1986, 1, 913-917.
14. Mignani, G.; Kramer, A.; Puccetti, G.; Ledoux, I.; Zyss, J.; Soula, G. Effect of a weak donor on the intramolecular charge-transfer of molecules containing 2 neighboring silicon atoms. Organometallics 1991, 10, 3656-3659.
15. Hartman, G. D.; Halczenko, W. A convenient synthesis of 4-aminomethyl-L-phenylalanine. Synth. Commun. 1991, 21, 2103-2107.
16. Bozell, J. J.; Vogt, C. E.; Gozum, J. Transition-metal-assisted asymmetric synthesis of amino acid analogues. A new synthesis of optically pure D- and L-pyridylalanines. J. Org. Chem., 1991, 56, 2584-2587.
17. Terauchi, K.; Sakurai, H. Photochemical studies of the esters of aroylphosphonic acids. Bull. Chem. Soc. Jpn. 1970, 43, 883-890.
18. Scherer, H.; Hartmann, A.; Regitz, M.; Tunggall, B. D.; Gunther, H. 7-Phosphono-7-aryl-norcaradiene. Chem. Ber. 1972, 105, 3357-3381.

What is claimed is:

1. A method of preparing δ,δ-difluorophosphonates from corresponding benzylic ketophosphonates, the method comprising:

reacting a ketophosphonate of the following Formula III'

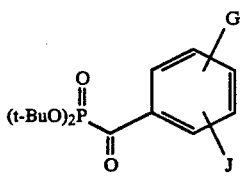

with a nucleophilic fluorinating agent, to yield an α,α-difluorophosphonate of the following Formula IV'

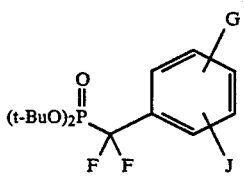

wherein G and J are non-reaction interfering moieties.

2. The method of claim 1, wherein the nucleophilic fluorinating agent comprises (diethylamino) sulfur trifluoride.

3. The method of claim 1, wherein G and J do not contain acidic substituents, hydroxy substituents, ketone substituents in their free form, or aldehyde substituents in their free form.

4. The method of claim 1, wherein the substituents G and J are the same or different and are selected from the group consisting of hydrogen, halogen, $C_{1-8}$ alkyl, and halogen substituted $C_{1-8}$ alkyl.

5. The method of claim 1, wherein the ketophosphonate compound of Formula III' is reacted with (diethylamino)sulfur trifluoride at a temperature of from about 20°-25° C. to yield the α,α-difluorophosphonate of Formula IV'.

6. The method of claim 1, wherein the ketophosphonate of Formula III' is prepared by oxidizing a corresponding α-hydroxyphosphonate of Formula II':

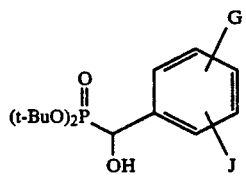

wherein G and J are the same or different and are non-reaction interfering moieties.

7. The method of claim 6, wherein G and J do not contain acidic substituents, ketone substituents in their free form, aldehyde substituents in their free form or unprotected hydroxy substituents.

8. The method of claim 6, wherein the compound of Formula II' is oxidized with an oxidizing agent selected from the group consisting of $MnO_2$, pyridinium dichromate, dichlorodicyanobenzoquinone, and a Swern oxidation agent.

* * * * *

UNITED STATES PATENT AND TRADEMARK OFFICE
CERTIFICATE OF CORRECTION

PATENT NO. : 5,264,607

DATED : November 23, 1993

INVENTOR(S) : Burke, Jr. et al.

Page 1 of 2

It is certified that error appears in the above-indentified patent and that said Letters Patent is hereby corrected as shown below:

On the title page, item [54] and column 1, lines 3 and 4, change "α,α-DIFLUROPHOSPHONATES" to --α,α-DIFLUOROPHOSPHONATES--; change "α-KETOPHOSPHORATES" to --α-KETOPHOSPHONATES--.

COLUMN 2, line 65, change "R" to --F--.

COLUMN 6, line 4, change "lo" to --10--;
line 20, change "4 [Bis(t-butyl)phosphonomethyl]-N-Fmoc-DL" to --4 [Bis(t-butyl)phosphonomethyl]-N-Fmoc-DL- --;
line 27, delete first occurrence of "to";
line 31, change "H$_{2/10\%}$" to --H$_2$/10%--.

COLUMN 8, line 27, change "Difluoroohosohonates" to --Difluorophosphonates--.

COLUMN 9, line 47, change "3," to --3',--.

COLUMN 11, line 56, change NEt$_3$1.22" to --NEt$_3$(1.22--.

COLUMN 12, line 22, change "(diethylamino)sulfu trifluoride" to --(diethylamino)sulfur trifluoride--;
line 31, change "Was" to --was--;
line 56, change "CHCl'" to --CHCl$_3$--.

COLUMN 16, line 56, change "4-[bis(tert-Butyl)phosphoryloarbonyl]-bromobenzene" to --4-[bis(tert-Butyl)phosphorylcarbonyl]-bromobenzene--;
line 67, change "z6" to --26--.

UNITED STATES PATENT AND TRADEMARK OFFICE
CERTIFICATE OF CORRECTION

PATENT NO. : 5,264,607
DATED : November 23, 1993
INVENTOR(S) : Burke, Jr. et al.

It is certified that error appears in the above-indentified patent and that said Letters Patent is hereby corrected as shown below:

COLUMN 17, line 1, change "4-[bie(tert-Butyl)phosphoryl" to --4-[bis(tert-Butyl)phosphoryl--;
line 9, before "32.7 g," insert --(--;
line 12, change "NaHCO," to --NaHCO$_3$--;
line 20, change "z7" to --27--;
line 21, change "C." to --C--;

COLUMN 18, claim 1, line 67, change "$\delta,\delta$-difluorophosphonates" to --$\alpha,\alpha$-difluorophosphonates--.

Signed and Sealed this

Twenty-fifth Day of October, 1994

Attest:

BRUCE LEHMAN

Attesting Officer    Commissioner of Patents and Trademarks